US009675285B2

United States Patent
Christian

(10) Patent No.: US 9,675,285 B2
(45) Date of Patent: Jun. 13, 2017

(54) DELIVERY DEVICE FOR IMPLANTABLE MONITOR

(75) Inventor: Steven C. Christian, New Brighton, MN (US)

(73) Assignee: GIVEN IMAGING LTD., Yoqneam (IL)

( * ) Notice: Subject to any disclaimer, the term of this patent is extended or adjusted under 35 U.S.C. 154(b) by 3187 days.

(21) Appl. No.: 11/740,163

(22) Filed: Apr. 25, 2007

(65) Prior Publication Data

US 2008/0091177 A1  Apr. 17, 2008

Related U.S. Application Data

(60) Provisional application No. 60/851,986, filed on Oct. 16, 2006.

(51) Int. Cl.
| | | |
|---|---|---|
| A61B 5/07 | (2006.01) | |
| A61B 5/145 | (2006.01) | |
| A61B 1/04 | (2006.01) | |
| A61B 5/00 | (2006.01) | |

(52) U.S. Cl.
CPC ........ *A61B 5/14539* (2013.01); *A61B 5/0031* (2013.01); *A61B 5/076* (2013.01); *A61B 5/6861* (2013.01); *A61B 1/041* (2013.01); *A61B 5/07* (2013.01); *A61B 5/6847* (2013.01)

(58) Field of Classification Search
CPC ......... A61B 5/07; A61B 5/076; A61B 5/6861; A61B 5/6847
USPC .......................................... 600/300, 301, 309
See application file for complete search history.

(56) References Cited

U.S. PATENT DOCUMENTS

| | | | |
|---|---|---|---|
| 3,133,537 A | 5/1964 | Muth | |
| 3,340,866 A | 9/1967 | Noller | |
| 3,480,003 A | 11/1969 | Crites | |
| 3,739,279 A | 6/1973 | Hollis | |
| 3,779,237 A | 12/1973 | Goeltz et al. | |

(Continued)

FOREIGN PATENT DOCUMENTS

| | | |
|---|---|---|
| WO | WO 98/02209 | 1/1998 |
| WO | WO 01/12102 A1 | 2/2001 |

(Continued)

OTHER PUBLICATIONS

Notification of Transmittal of the International Search Report and the Written Opinion of the International Searching Authority, or the Declaration, for corresponding patent applicatin No. PCT/US2007/081521, mailed Apr. 9, 2008, (17 pages).

*Primary Examiner* — Patricia Mallari
*Assistant Examiner* — Karen Toth
(74) *Attorney, Agent, or Firm* — Pearl Cohen Zedek Latzer Baratz LLP

(57) ABSTRACT

In general, this disclosure describes techniques for placing a capsule for sensing one or more parameters of a patient. In particular, the techniques provide for anchoring of the capsule to a tissue at a specific site and releasing the capsule from the device using a single actuator. As an example, a delivery device may anchor the capsule to the tissue site during a first motion of the actuator and release the capsule from the delivery device during a second motion of the actuator. This allows a user to place the capsule by interacting with only a single actuator, thus making delivery of the capsule easier and more reliable.

35 Claims, 11 Drawing Sheets

(56) References Cited

U.S. PATENT DOCUMENTS

| | | | |
|---|---|---|---|
| 3,949,388 A | 4/1976 | Fuller | |
| 4,030,481 A | 6/1977 | Hill | |
| 4,062,360 A | 12/1977 | Bentley | |
| 4,257,420 A | 3/1981 | Terayama | |
| 4,326,535 A | 4/1982 | Steffel et al. | |
| 4,503,859 A | 3/1985 | Petty et al. | |
| 4,546,436 A | 10/1985 | Schneider et al. | |
| 4,561,450 A | 12/1985 | Bryant | |
| 4,618,929 A | 10/1986 | Miller et al. | |
| 4,638,045 A | 1/1987 | Kohn et al. | |
| 4,748,562 A | 5/1988 | Miller et al. | |
| 4,823,808 A | 4/1989 | Clegg et al. | |
| 4,924,877 A | 5/1990 | Brooks | |
| 4,967,759 A | 11/1990 | Teves | |
| 4,981,470 A | 1/1991 | Bombeck, IV | |
| 4,991,590 A | 2/1991 | Shi | |
| 5,018,529 A | 5/1991 | Tenerz et al. | |
| 5,063,081 A | 11/1991 | Cozzette et al. | |
| 5,080,663 A | 1/1992 | Mills et al. | |
| 5,105,812 A | 4/1992 | Corman | |
| 5,108,889 A | 4/1992 | Smith | |
| 5,117,827 A | 6/1992 | Stuebe et al. | |
| 5,127,404 A | 7/1992 | Wyborny et al. | |
| 5,153,584 A | 10/1992 | Engira | |
| 5,247,938 A | 9/1993 | Silverstein et al. | |
| 5,269,789 A | 12/1993 | Chin et al. | |
| 5,297,437 A | 3/1994 | Schneider | |
| 5,301,673 A | 4/1994 | Rabito et al. | |
| 5,339,799 A | 8/1994 | Kami et al. | |
| 5,368,027 A | 11/1994 | Lubbers et al. | |
| 5,381,800 A | 1/1995 | Angelchik | |
| 5,394,882 A | 3/1995 | Mawhinney | |
| 5,398,844 A | 3/1995 | Zaslavsky et al. | |
| 5,411,022 A | 5/1995 | McCue et al. | |
| 5,479,935 A | 1/1996 | Essen-Moller | |
| 5,486,818 A | 1/1996 | Loponen | |
| 5,497,772 A | 3/1996 | Schulman et al. | |
| 5,624,453 A | 4/1997 | Ahmed | |
| 5,697,384 A | 12/1997 | Miyawaki et al. | |
| 5,720,771 A | 2/1998 | Snell | |
| 5,759,199 A | 6/1998 | Snell et al. | |
| 5,792,153 A | 8/1998 | Swain et al. | |
| 5,833,625 A | 11/1998 | Essen-Moller | |
| 5,836,895 A | 11/1998 | Ramsey, III | |
| 5,843,139 A | 12/1998 | Goedeke et al. | |
| 5,862,803 A | 1/1999 | Besson et al. | |
| 5,873,369 A | 2/1999 | Laniado et al. | |
| 5,899,931 A | 5/1999 | Deschamp et al. | |
| 5,935,078 A | 8/1999 | Feierbach | |
| 5,957,854 A | 9/1999 | Besson et al. | |
| 5,984,875 A | 11/1999 | Brune | |
| 6,088,608 A | 7/2000 | Schulman et al. | |
| 6,113,553 A | 9/2000 | Chubbuck | |
| 6,190,353 B1 | 2/2001 | Makower et al. | |
| 6,285,897 B1 | 9/2001 | Kilcoyne et al. | |
| 6,285,899 B1 | 9/2001 | Ghaem et al. | |
| 6,304,766 B1 | 10/2001 | Colvin, Jr. | |
| 6,358,197 B1 * | 3/2002 | Silverman et al. | 600/29 |
| 6,398,710 B1 | 6/2002 | Ishikawa et al. | |
| 6,402,689 B1 | 6/2002 | Scarantino et al. | |
| 6,406,498 B1 | 6/2002 | Tormala et al. | |
| 6,409,674 B1 | 6/2002 | Brockway et al. | |
| 6,416,471 B1 | 7/2002 | Kumar et al. | |
| 6,585,644 B2 | 7/2003 | Lebel et al. | |
| 6,632,175 B1 | 10/2003 | Marshall | |
| 6,689,056 B1 | 2/2004 | Kilcoyne et al. | |
| 6,951,536 B2 | 10/2005 | Yokoi et al. | |
| 6,994,712 B1 | 2/2006 | Fisher et al. | |
| 7,052,474 B2 | 5/2006 | Castell et al. | |
| 7,371,215 B2 * | 5/2008 | Colliou et al. | 600/300 |
| 7,448,993 B2 * | 11/2008 | Yokoi et al. | 600/114 |
| 7,479,108 B2 * | 1/2009 | Rini et al. | 600/300 |
| 7,621,036 B2 * | 11/2009 | Cros et al. | 29/595 |
| 7,654,985 B2 * | 2/2010 | Dinsmoor et al. | 604/174 |
| 8,219,171 B2 * | 7/2012 | Benoist | A61B 5/076 600/343 |
| 2003/0171664 A1 * | 9/2003 | Wendlandt | 600/407 |
| 2004/0133089 A1 | 7/2004 | Kilcoyne et al. | |
| 2004/0158125 A1 | 8/2004 | Aznoian et al. | |
| 2004/0158138 A1 * | 8/2004 | Kilcoyne et al. | 600/350 |
| 2004/0215128 A1 * | 10/2004 | Eerdmans | 604/27 |
| 2004/0260164 A1 | 12/2004 | Kilcoyne et al. | |
| 2005/0165272 A1 | 7/2005 | Okada et al. | |
| 2005/0165419 A1 * | 7/2005 | Sauer et al. | 606/148 |
| 2005/0209653 A1 | 9/2005 | Herbert et al. | |
| 2005/0288555 A1 | 12/2005 | Binmoeller | |
| 2006/0247724 A1 | 11/2006 | Gerber et al. | |
| 2009/0209815 A1 * | 8/2009 | Smith et al. | 600/114 |
| 2010/0131016 A1 * | 5/2010 | Gerber et al. | 606/304 |

FOREIGN PATENT DOCUMENTS

WO    WO 02/087657 A2    11/2002
WO    WO 2006/099425 A1    9/2006

* cited by examiner

DELIVERY DEVICE FOR IMPLANTABLE MONITOR

This application claims the benefit of U.S. Provisional Application No. 60/851,986, filed Oct. 16, 2006, the entire content of each of which is incorporated herein by reference.

TECHNICAL FIELD

This disclosure relates to medical devices and, more particularly, to medical devices for monitoring physiological conditions within a body lumen.

BACKGROUND

Gastroesophageal reflux occurs when stomach acid intermittently surges into the esophagus. It is common for most people to experience this acid reflux occasionally as heartburn. Gastroesophageal reflux disease (GERD) is a clinical condition in which the reflux of stomach acid into the esophagus is frequent enough and severe enough to impact a patient's normal functioning or to cause damage to the esophagus.

In the lower part of the esophagus, where the esophagus meets the stomach, there is a muscular valve called the lower esophageal sphincter (LES). Normally, the LES relaxes to allow food to enter into the stomach from the esophagus. The LES then contracts to prevent stomach acids from entering the esophagus. In GERD, the LES relaxes too frequently or at inappropriate times, allowing stomach acids to reflux into the esophagus.

The most common symptom of GERD is heartburn. Acid reflux also leads to esophageal inflammation, which causes symptoms such as painful swallowing and difficulty swallowing. Pulmonary symptoms such as coughing, wheezing, asthma, or inflammation of the vocal cords or throat may occur in some patients. More serious complications from GERD include esophageal ulcers and narrowing of the esophagus. The most serious complication from chronic GERD is a condition called Barrett's esophagus in which the epithelium of the esophagus is replaced with abnormal tissue. Barrett's esophagus is a risk factor for the development of cancer of the esophagus.

Accurate diagnosis of GERD is difficult but important. Accurate diagnosis allows identification of individuals at high risk for developing the complications associated with GERD. It is also important to be able to differentiate between gastroesophageal reflux, other gastrointestinal conditions, and various cardiac conditions. For example, the similarity between the symptoms of a heart attack and heartburn often lead to confusion about the cause of the symptoms. Esophageal manometry, esophageal endoscopy, and esophageal pH monitoring are standard methods of measuring esophageal exposure to stomach acids and are currently used to diagnose GERD.

SUMMARY

In general, this disclosure describes techniques for placing a capsule used for sensing one or more parameters within a body lumen of a patient. A delivery device may be configured to anchor the capsule to tissue at a specific site within the body lumen during a first motion of an actuator and release the capsule from the delivery device during a second motion of the actuator. In this manner, a user may place the capsule by interacting with a single actuator.

In one embodiment, a device comprises an elongated probe configured to carry an implantable capsule for deployment within a patient, an anchor element configured to anchor the capsule to tissue within the patient, a release mechanism configured to release the capsule from the probe, and an actuator configured to activate the anchor element to cause the anchor element to anchor the capsule to the tissue during a first motion of the actuator, and activates the release mechanism to release the capsule from the probe during a second motion of the actuator.

In another embodiment, a method comprises anchoring an implantable capsule to tissue within a patient during a first motion of an actuator of a device and releasing the capsule from the device during a second motion of the actuator.

In a further embodiment, a device comprises means for carrying an implantable capsule for deployment within a patient, means for anchoring the capsule to tissue within the patient, means for releasing the capsule from the carrying means, and means for activating the anchoring means to anchor the capsule to the tissue during a first motion of the activating means and activating the releasing means to release the capsule from the carrying means during a second motion of the activating means.

In another embodiment, a system comprises a delivery apparatus that includes an elongated probe configured to carry an implantable capsule for deployment within a patient, a release mechanism configured to release the capsule from the probe and an actuator, and an actuator to control delivery of the capsule. The system further includes an anchor element configured to anchor the capsule to tissue within the patient. The actuator is configured to activate the anchor element to cause the anchor element to anchor the capsule to the tissue during a first motion of the actuator, and activates the release mechanism to release the capsule from the probe during a second motion of the actuator.

The details of one or more embodiments are set forth in the accompanying drawings and the description below. Other features, objects, and advantages of the described techniques will be apparent from the description and drawings, and from the claims.

DETAILED DESCRIPTION

In general, this disclosure describes techniques for placing an implantable capsule used for sensing one or more parameters within a body lumen of a patient. A delivery device may be configured to anchor the capsule to tissue at a specific site within the body lumen during a first motion of an actuator and release the capsule from the delivery device during a second motion of the actuator. In this manner, a user may place the capsule by interacting with a single actuator.

Figure 1:
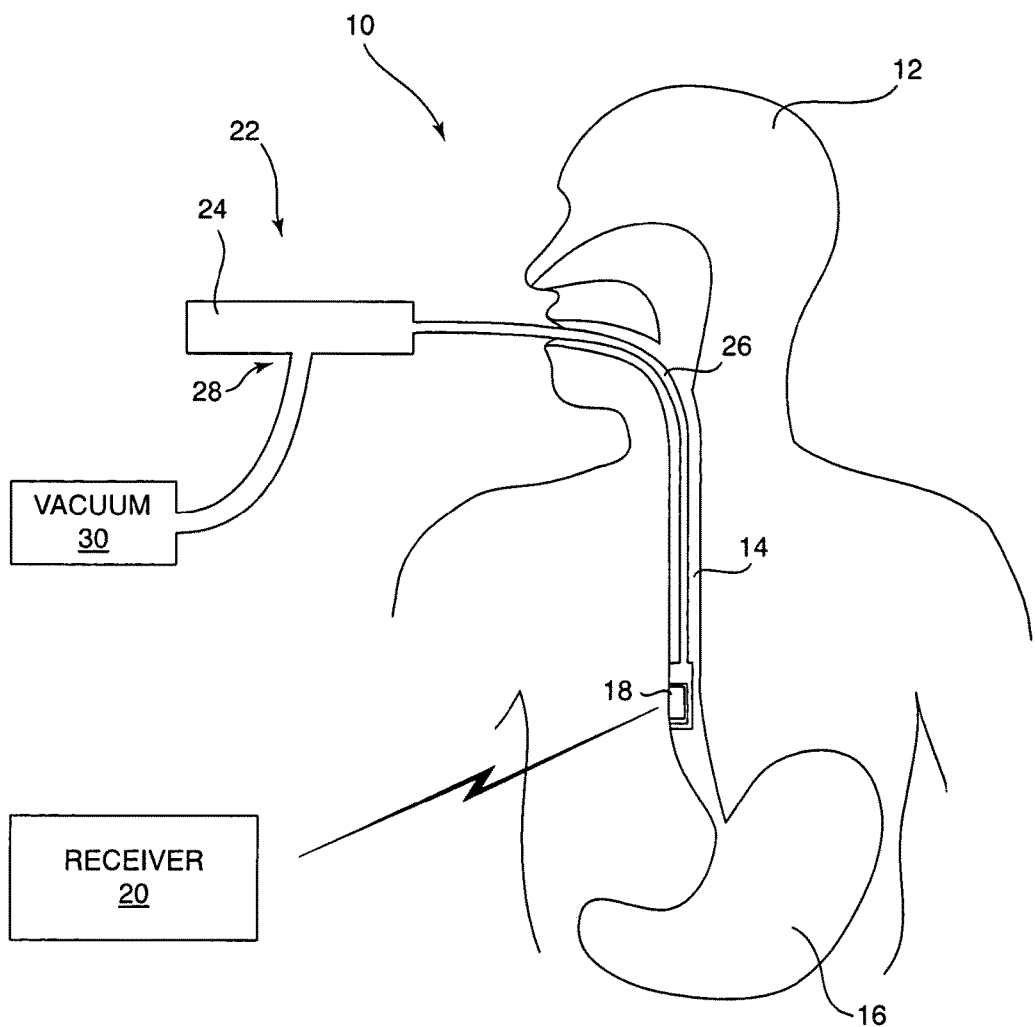
FIG. 1 is a schematic diagram illustrating an esophageal acidity monitoring system shown in conjunction with a patient.

FIG. 1 is a schematic diagram illustrating an acidity monitoring system 10 shown in conjunction with a patient 12. Acidity monitoring system 10 measures the acidity within the lower portion of an esophagus 14 of patient 12. More specifically, acidity monitoring system 10 measures the acidity level near the lower esophageal sphincter (LES) of patient 12, i.e., where esophagus 14 meets stomach 16. Measuring the acidity level of the lower portion of esophagus 14 allows a physician to more accurately diagnose Gastroesophageal Reflux Disease (GERD). Although system 10 is described in this disclosure in terms of sensing acidity in the esophagus, the system may be adapted for application to a variety of other sensing environments, and to a variety of different sensing applications. In other words, system 10 may be used for monitoring other locations within patient 12 or monitoring other body parameters.

As described above, the LES normally relaxes to allow food to enter into stomach 16 from esophagus 14. The LES then contracts to prevent stomach contents from entering esophagus 14. In GERD, the LES relaxes too frequently or at inappropriate times allowing stomach contents to reflux into the esophagus 14, increasing the acidity level near the lower portion of esophagus 14, which may lead to complications such as heartburn, painful swallowing, difficulty swallowing, coughing, wheezing, asthma, inflammation of the vocal cords or throat, esophageal ulcers, narrowing of the esophagus, and in the worst cases Barrett's esophagus.

Acidity monitoring system 10 includes a capsule 18 for sensing acidity. Capsule 18 includes an acidity sensor, e.g., a pH sensor (not shown), to measure the acidity level within esophagus 14. The pH sensor carried by capsule 18 may generally conform to the pH sensor employed in monitoring devices, such as those described in U.S. Pat. Nos. 6,285,897 and 6,689,056 to Kilcoyne et al., the entire content of which may be incorporated herein by reference. Capsule 18 may be in wireless communication with a receiver 20. Thus, capsule 18 may transmit measured acidity data to receiver 20 via a transmitter and an antenna (not shown). Receiver 20 may, for example, comprise a portable receiver that is carried by patient 12. The information stored within receiver 20 may be downloaded by a physician to a computing device and analyzed to diagnose the condition of patient 12. Alternatively, capsule may include a memory that stores the measured data, thus permitting recovery of the data after capsule 18 is passed through patient 12.

A delivery device 22 attaches capsule 18 to a wall of esophagus 14 and, more particularly, to esophageal tissue within esophagus 14. Delivery device 22 includes a proximal portion, referred to herein as a handle 24, and an elongated probe 26 that extends from handle 24 into esophagus 14 of patient 12. Elongated probe 26 is configured to carry capsule 18 for deployment within patient 12. Capsule 18 may, for example, be coupled to a distal end of delivery device 22 for delivery to a particular location within esophagus 14. As will be described in detail below, delivery device 22 may utilize a single actuator, such as a drive wire (not shown), to both anchor capsule 18 to esophagus 14 in a first motion and release the capsule from delivery device 22 in a second motion.

In the example of FIG. 1, delivery device 22 includes a vacuum inlet 28 on handle 24 to couple delivery device 22 to a vacuum 30. Vacuum 30 applies suction within an inner lumen formed by probe 26. A vacuum outlet (not shown) at the distal end of probe 26 and, more particularly, at the interface between probe 26 and capsule 18, applies the suction from vacuum 30 to the wall of esophagus 14 in order to draw esophageal tissue into a void within capsule 18. Delivery device 22 anchors capsule 18 to the esophageal tissue drawn into the void of capsule 18 and disengages from capsule 18, thereby leaving capsule 18 attached to the wall of esophagus 14.

In particular, the actuator is configured to activate an anchor element during a first motion to anchor capsule 18 to the wall of esophagus 14. The actuator is also configured to activate a release mechanism during a second motion to cause a retention mechanism coupled to capsule 18 to detach from capsule 18, thus releasing capsule 18 from delivery device 22. In some embodiments, the first motion and second motion may be movement in substantially opposite directions. For example, the actuator may activate the anchor element during a forward motion and activate a release mechanism during a rearward motion. In other embodiments, the first and second motion may be movement in substantially the same direction. For example, the actuator may activate an anchor element during a forward motion to a first position and activate the release mechanism during a forward motion to a second position. Allowing the physician to place capsule 18 with a single actuator, in accordance with this disclosure, may make the delivery system more reliable and easier to operate. Additionally, the delivery system may be less costly to produce.

While on the wall of esophagus 14, the acidity sensor of capsule 18 obtains acidity measurements for a period of time, e.g., several hours or several days, and relays the acidity measurements to receiver 20 via wireless telemetry. Capsule 18 eventually detaches from the wall of the esophagus and is passed through the digestive system of patient 12. For some applications, however, in the esophagus or in other body lumens, tissue sites, or organs, capsule 18 may be designed for more persistent placement, such that the capsule may remain attached within the patient for several weeks, months, or possibly years.

Although the techniques of this disclosure are described in terms of delivering a capsule 18 for sensing acidity of esophagus 14 of the patient, the techniques of the disclosure may be applied for delivery of other types of sensors to different tissue locations or organs. Moreover, the techniques of this disclosure may be used to place other therapeutic devices, drugs or other agents to locations within patient 12.

Figure 2:
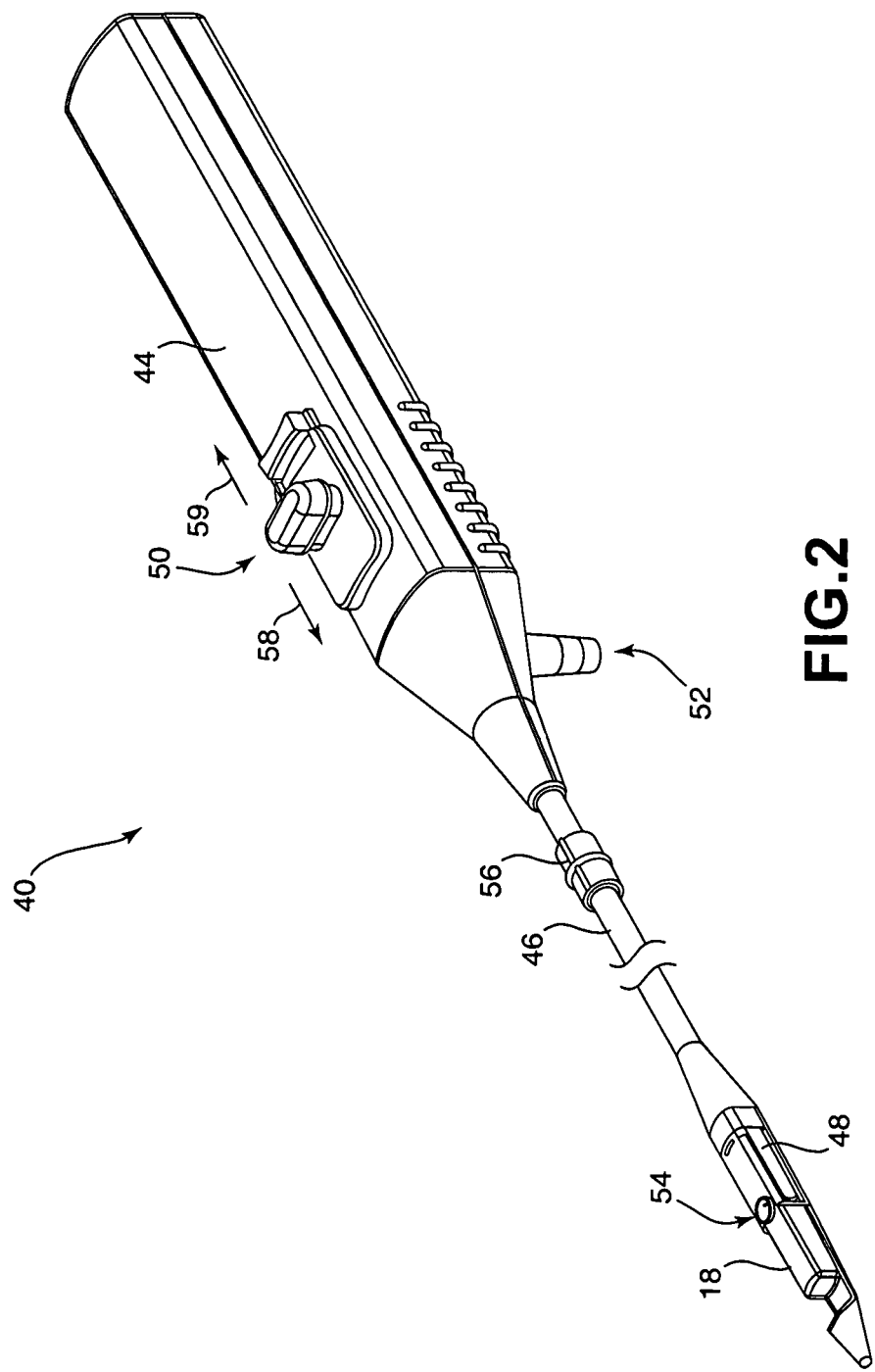
FIG. 2 is a perspective diagram illustrating an exemplary delivery device for placing a capsule at a location within body lumen of a patient.

FIG. 2 is a schematic diagram illustrating an exemplary delivery device 40 for delivering a capsule 18 to a location within a patient, substantially as shown in FIG. 1. Delivery device 40 includes a handle 44 and an elongated probe 46 that extends from handle 44. Delivery device 40 also includes a capsule coupling mechanism 48 at a distal end of probe 46 that is coupled to capsule 18 to secure capsule 18 to delivery device 40 during placement of capsule 18. Delivery device 40 places capsule 18 at an appropriate tissue location along esophagus 14 (FIG. 1), anchors capsule 18 to the appropriate location during a first motion of an actuator and releases capsule 18 during a second motion of the actuator. In this manner, delivery device 40 is capable of anchoring capsule 18 to a tissue location and releasing capsule 18 from delivery device 40 using a single actuator. In one embodiment, the actuator may comprise a drive wire.

Delivery device 40 includes a controller 50 located on handle 44 that controls operation of the actuator, e.g., drive wire, to anchor capsule 18 to the wall of esophagus 14 and release capsule 18 from delivery device 40. Controller 50 may comprise a sliding button that is successively pushed through different stages to perform sequential operations during the delivery of capsule 18 to the appropriate location along esophagus 14. Alternatively, controller 50 may comprise a dial, switch, or similar control mechanism that can be switched to different settings to perform different functions, e.g., by linear or rotational movement. In some embodiments, controller 40 may be manually activated, e.g., by a physician's hand, or automatically activate, e.g., by a motor or other drive mechanism in response to physician action.

The distal end of delivery device 40, which carries capsule 18, enters esophagus 14 and extends through esophagus 14 to a location five to six centimeters above the LES, i.e., the tissue location of interest in this example. The distal end of delivery device 40 may be guided to the LES using a number of different techniques. For example, delivery device 40 may detect a pressure variation, such as a pressure variation between the stomach and the esophagus, to identify the location of the LES. Alternatively, the user of delivery device 40 may use external imaging techniques, such as ultrasound or fluoroscopy, to track the location of the distal end of delivery device 40. In another embodiment, the distal end of delivery device 40 is inserted into patient 12 until a depth marker 56 reaches a particular location. Depth marker 56 may be moved up or down probe 46 based on the approximate length of esophagus 14 of patient 12.

Upon identifying the appropriate location for placement of capsule 18, delivery device opens vacuum inlet 52. Controller 50 may control opening and closing of vacuum inlet 52 and, thus, application of suction from vacuum 30 (FIG. 1). Controller 50 may open vacuum inlet 52 upon actuation of controller 50. Alternatively, the user of delivery device 40 may control application of the suction from vacuum 30 by turning on and off vacuum 30. Vacuum inlet 52 receives sufficient suction pressure from vacuum 30 to draw a portion of esophageal tissue into a void 54 of capsule 18.

Upon drawing the esophageal tissue into void 54, controller 50 is adjusted to cause delivery device 40 to anchor capsule 18 to the esophageal tissue drawn into void 54. In one embodiment, controller 50 may slide toward the distal end of delivery device 40, i.e., in a forward direction, to cause the drive wire to deploy an anchor element that is configured to anchor sensing capsule 18 to a wall of esophagus 14. For example, the drive wire may deploy a pin through the esophageal tissue when controller 50 is advanced in the forward motion. The forward motion is motion in the direction of arrow 58. Although a pin is described for purposes of illustration, other types of anchoring elements may be used. U.S. Pat. Nos. 6,285,897 and 6,689,056 to Kilcoyne et al. provide examples of a variety of anchoring elements for attaching monitoring devices to the lining of the esophagus. The anchoring elements described in the Kilcoyne et al. patents may be suitable for attachment of capsule 18.

After capsule 18 is anchored to the wall of esophagus 14, delivery device 40 releases capsule 18, thereby leaving capsule 18 attached to the wall of esophagus 14. Delivery device 40 may release capsule 18 during a rearward motion of the drive wire. The rearward motion is motion in the direction of arrow 59. In particular, when controller 50 slides in the rearward direction the drive wire activates a release mechanism that releases capsule 18 from delivery device 40. As an example, rearward motion of the drive wire may cause a retention mechanism, such as one or more prongs, within capsule coupling mechanism 48 to disengage from capsule 18, thus releasing capsule 18 from delivery device 40. In this manner, delivery device 40 anchors capsule 18 to the tissue and releases capsule 18 from delivery device 40 using a single actuator.

Delivery device 40 is then removed and a sensor of capsule 18 begins to measure one or more parameters of esophagus 14 over time and transmit the information to receiver 20 via wireless communication, e.g., via a transmitter and an antenna. As an example, the sensor of capsule 18 may measure one or more parameters that indicate an acidity of esophagus 14. Such operation is described above with respect to FIG. 1.

Figure 3:
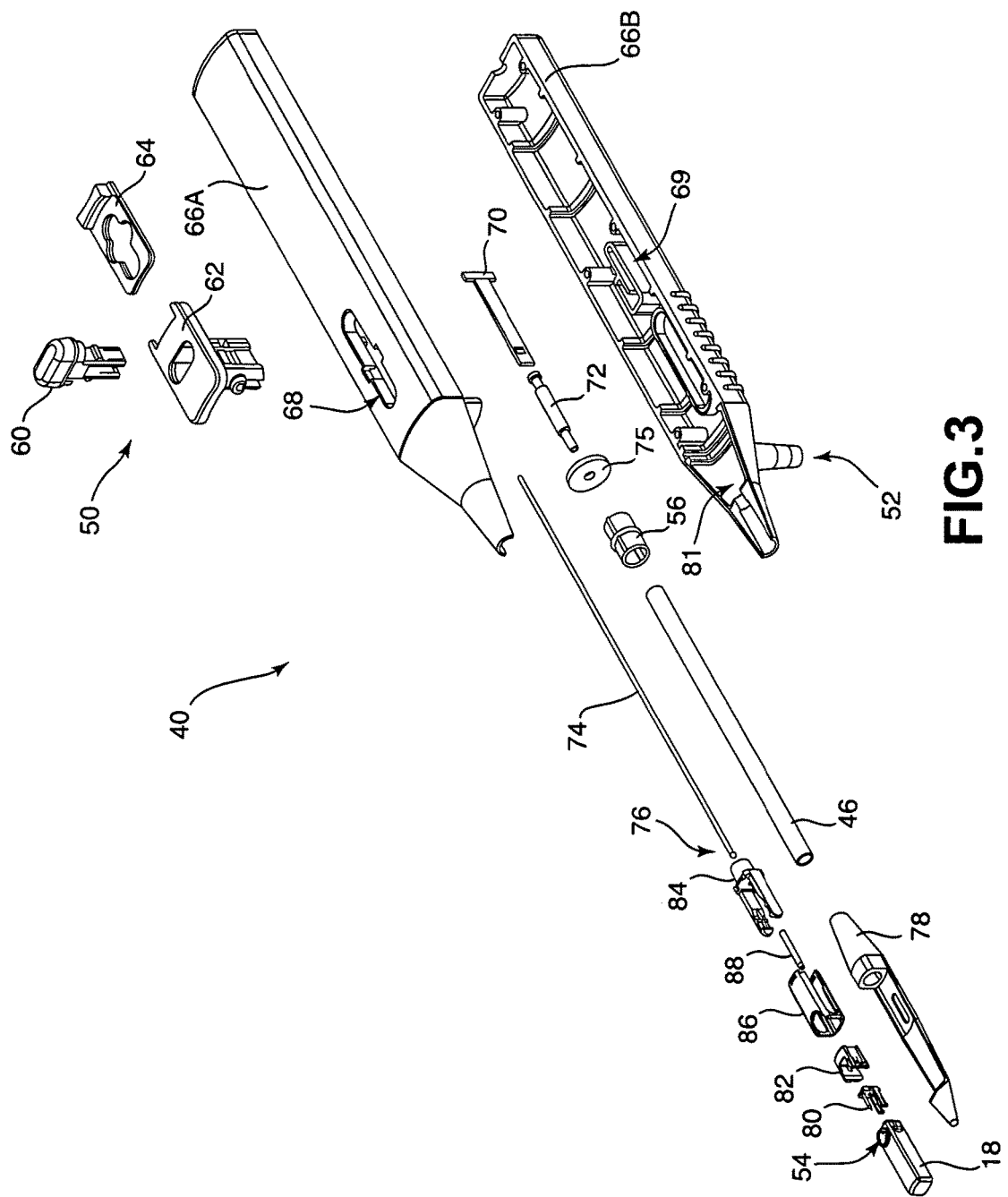
FIG. 3 is a schematic diagram illustrating an exploded view of the delivery device of FIG. 2.

FIG. 3 is a schematic diagram illustrating an exploded view of exemplary delivery device 40 of FIG. 2. The exploded view of delivery device 40 illustrates various example components of delivery device 40. Delivery device 40 includes a slider button 60, a slider 62 and a slider lock 64. Slider button 60 and slider 62 couple together to form a controller 50 (FIG. 2) that is successively placed in different positions to perform sequential control operations during delivery of capsule 18. Slider lock 64 locks controller 50 to prevent inadvertent movement of controller 50 during packing, shipping or unpacking. Hence, when slider lock 64 is coupled to controller 50, controller 50 is unable to move in any direction. Slider lock 64 is disengaged prior to use of delivery device 40.

Delivery device 40 further includes an upper handle body 66A and a lower handle body 66B. Upper handle body 66A and lower handle body 66B couple together to form handle 44 (FIG. 2). Upper handle body 66A is formed to include a slide groove 68. Slider button 60 and slider 62 fit into slide groove 68, and slide forward and backward in slide groove 68 in response to force applied by a user of the device.

Lower handle body 66B is formed to include a vacuum inlet 52 that couples to a vacuum (FIG. 1) to provide suction. Upper handle body 66A and lower handle body 66B are formed to include a groove 69. For simplicity, FIG. 3 only illustrates the portion of groove 69 formed in lower handle body 66B. However, upper handle body 66A also includes a similar groove portion. Groove 69 receives an element that slides within groove 69, such as a spring element 70. Groove 69 is formed to allow controller 50 to only move in the forward direction initially. For example, spring element 70 may fit into a first portion of groove 69 in a manner that prevents initial movement in the rearward direction. Thus, controller 50 is still unable to be move in a rearward direction after slide lock 64 is removed.

As will be described in detail, after controller 50 is initially moved forward, spring element 70 moves from the first portion of groove 69 into a second portion of groove 69. The second portion of groove 69 allows for movement in the rearward direction. In this manner, groove 69 and spring element 70 form a means for preventing inadvertent release of capsule 18 from delivery device 22 by preventing controller 50 from moving in the rearward direction until anchor element 80 is deployed. Although described in terms of a groove 69 and spring element 70, the means for preventing movement in the rearward direction until anchor element 80 is deployed may be realized using other mechanical or electromechanical mechanisms. For example, groove 69 may receive elements other than spring element 70.

Delivery device 40 also includes a drive wire adaptor 72. During forward motion of controller 50, drive wire adaptor 72 advances a drive wire 74 to anchor capsule 18 to the wall of esophagus 14. As illustrated in the example of FIG. 3, drive wire adaptor 72 is formed to have at least two sections of different diameters. A front portion of drive wire adaptor 72, i.e., the portion that interacts with drive wire 74, is of a smaller diameter than the main body of drive wire adaptor 72. The different diameter sections of drive wire adaptor 72 assist in creating a vacuum chamber within delivery device 40, as described below.

Initially, the larger diameter portion of drive wire adaptor 72 is located within a center of a seal 75. Thus, the larger diameter portion of drive wire adaptor 72 and seal 75 create a vacuum chamber within a forward region 81 of delivery device 40. In particular, the vacuum chamber extends from seal 75 through probe 46 and a vacuum channel 88 into a void 54 of capsule 18. Vacuum channel 88 may be integrated into one of the other elements of delivery device 40, such as within a capsule coupling housing 86, which is described below. While drive wire adaptor 72 is advanced forward to anchor capsule 18, the larger diameter portion of drive wire adaptor 72 remains seated within the central aperture of seal 75, maintaining the vacuum seal. Upon the rearward motion of controller 50, however, drive wire adaptor 72 retracts from seal 75 until the smaller diameter portion of drive wire adaptor 72 is located within the center of seal 75. The smaller diameter portion of drive wire adaptor 72 does not fill the entire central aperture of seal 75. When this occurs, the vacuum chamber within delivery device 40 is vented, thus reducing the suction force caused by the attached vacuum 30 (FIG. 1).

Drive wire 74 is located within an inner lumen formed by probe 46, and runs the length of delivery device 40. The length of probe 46 and drive wire 74 may be much longer than they appear in FIG. 3. As an example, probe 46 and drive wire 74 may be approximately twenty to thirty inches (fifty to seventy-five centimeters). Drive wire 74 and probe 46, however, are illustrated in FIG. 3 in shorter lengths for ease of illustration. A depth marker 56 may be adjusted along probe 46 to measure a length of probe 46 for insertion into a patient 12. Drive wire 74 includes a protrusion, such as a ball portion 76, located at the distal end of drive wire 74. Ball portion 76 is constructed such that during rearward motion, ball portion 76 engages with a release mechanism to release capsule 18 from delivery device 40 as described below. Although the protrusion at the distal end of drive wire 74 is shaped like a ball, the protrusion may take other forms such as a square, a T-shape or the like.

The distal portion of delivery device 40 includes a nose 78. Nose 78 couples to an anchor element 80, a release mechanism 82 and a capsule coupling mechanism 84. Capsule coupling mechanism 84 fits into a capsule coupling housing 86. As illustrated in FIG. 3, capsule coupling mechanism 84 includes a retention mechanism, such as one or more prongs, that couple to capsule 18. As will be described in detail, the prongs of capsule coupling mechanism 84 engage with channel-like detents formed on capsule 18 to securely couple capsule 18 to delivery device 40 during delivery to a tissue location.

Anchor element 80 is configured to anchor capsule 18 to tissue that is suctioned into void 54. Anchor element 80 anchors capsule 18 to the tissue in void 54 during forward motion of controller 50. As an example, anchor element 80 may comprise a locking pin that is driven through the tissue in void 54 in response to forward motion of controller 50. More specifically, the forward motion of controller 50 causes drive wire 74 to advance forward to drive the locking pin through the tissue suctioned into void 54 of capsule 18. As described above, other type of anchor elements may be used in place of the locking pin.

After capsule 18 is anchored to the tissue, drive wire 74 engages release mechanism 82, which is configured to release capsule 18 from delivery device 40. In the example illustrated in FIG. 3, release mechanism 82 comprises a cam that interacts with capsule coupling mechanism 84 to release capsule 18. In particular, an enlarged portion of drive wire 74, such as ball portion 76, engages with the cam during rearward motion to cause the cam to retract towards handle 44. As will be described in detail herein, the retraction of the cam toward handle 44 causes the prongs of capsule coupling mechanism 84 to expand outwards to release capsule 18. In this manner, the cam acts as a release mechanism that releases capsule 18 from delivery device 40.

Figure 4:
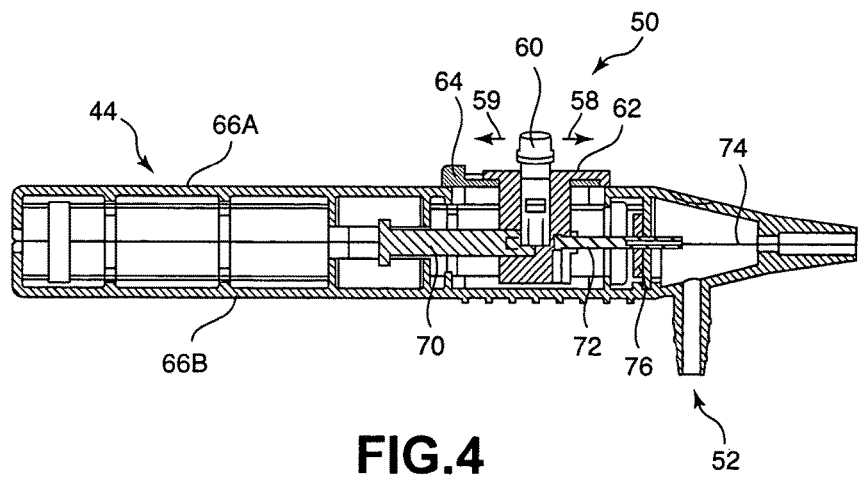
FIG. 4 is a cross-sectional side view of a handle portion of the delivery device of FIG. 2.

FIG. 4 is a cross-sectional view of a side of a handle 44 of exemplary delivery device 40. A user of delivery device 40 interacts with controller 50 of handle 44 to anchor capsule 18 to the tissue location of interest and to release capsule 18 from delivery device 40. Initially, controller 50 is located in a position such that the only direction in which controller 50 may be moved is in a forward direction. Spring element 70 may, for example, be aligned in a first channel of groove 69 in order to only permit movement of controller 50 in the forward direction. At this initial position, the larger diameter portion of drive wire adaptor 72 is located within a center of a seal 75 as illustrated in FIG. 4. The larger diameter portion of drive wire adaptor 72 and seal 75 create a vacuum chamber within delivery device 40. In particular, the vacuum chamber extends from seal 75 through probe 26 and vacuum channel 88 (FIG. 3) into a void 54 of capsule 18.

A vacuum chamber may be formed when the first section of the drive wire adaptor is seated in the central aperture and vented when the second section of the drive wire is seated in the central aperture.

After suction is applied to draw tissue into void 54 of capsule 18, slide button 60 and slider 62 move in the forward direction pushing drive wire adaptor 72 forward. In turn, drive wire adaptor 72 advances drive wire 74 forward. The advancement of drive wire 74 causes an anchor element to anchor capsule 18 to the tissue within void 54. In this position, the larger diameter portion of drive wire adaptor 72 still remains within seal 75 and thus the vacuum chamber is still intact.

After controller 50 is initially moved forward, spring element 70 moves into a second channel of groove 69 that allows for movement of controller 50 in a rearward direction further along handle than the original position of controller 50. During movement in the rearward direction, drive wire adaptor 72 causes drive wire 74 to retract toward handle 44 of delivery device 40. Drive wire 74 engages release mechanism 82 (FIG. 3) while moving in the rearward direction, causing the capsule coupling mechanism 84 (FIG. 3) to release the capsule 18.

Additionally, the movement of controller 50 in the rearward direction causes retraction of drive wire adaptor 72 until the smaller diameter portion of drive wire adaptor 72 is located within the center of seal 75. When this occurs, the vacuum chamber within delivery device 40 is vented, thus redirecting the suction force caused by the attached vacuum 30 (FIG. 1). At this point, the amount of suction that is being applied is small enough to allow release of capsule 18. In other embodiments, the suction force caused by the attached vacuum 30 may be manually controlled by the user of delivery device 40.

Figures 5A, 5B, 5C:
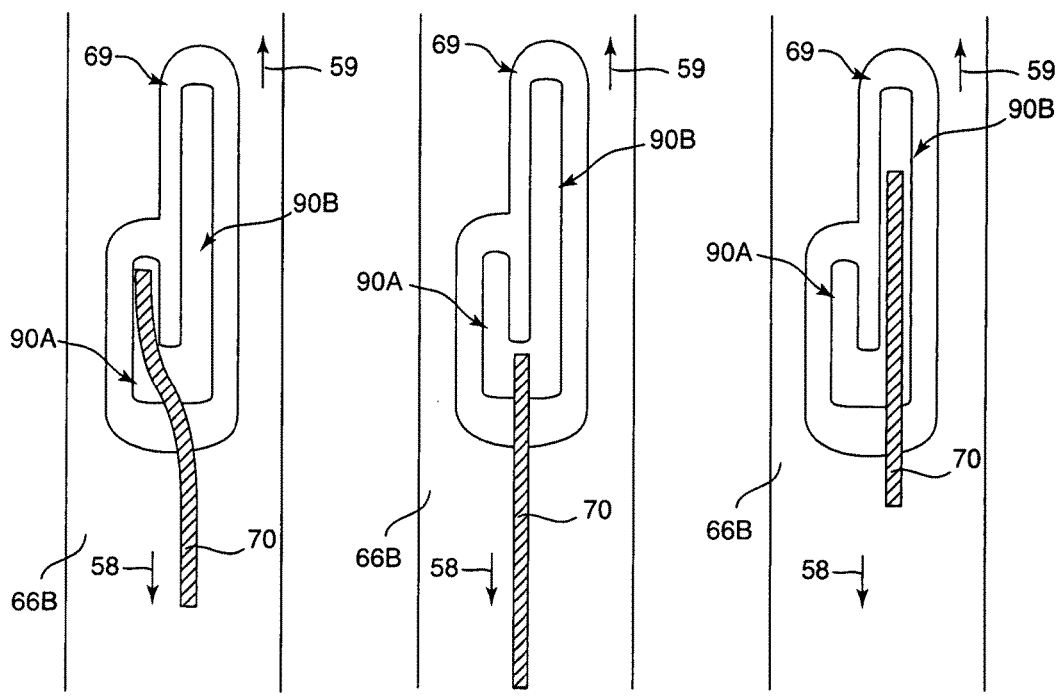
FIGS. 5A-5C are top views illustrating an exemplary locking structure for preventing inadvertent release of a capsule from a delivery device such as that shown in FIGS. 2-4.

FIGS. 5A-5C are schematic diagrams illustrating exemplary operation of spring element 70 within groove 69 to prevent inadvertent release of capsule 18. In particular, FIGS. 5A-5C illustrate a groove 69 formed in a lower handle body 66B of delivery device 40, and the interaction between groove 69 and spring element 70 to prevent inadvertent release of capsule 18. As described above, upper handle body 66A also includes a similar groove portion which interacts with a spring element 70 in a similar manner.

Groove 69 includes a first groove channel 90A and a second groove channel 90B. As illustrated in detail in FIGS. 5A-5C, first groove channel 90A is shorter than second groove channel 90B. In other words, second groove channel 90B extends further in the rearward direction (represented by arrow 59) than first groove channel 90A. Arrow 59 points in the opposite direction of elongated probe 46 (FIG. 2). FIG. 5A shows the initial position of spring element 70 within the groove 69. Spring element 70 is initially positioned within first groove channel 90A. Because first groove channel 90A is shorter than second groove channel 90B, spring element 70 is prevented from initially moving in the rearward direction. Controller 50, which is coupled to spring element 70, is therefore also prevented from initially moving in the rearward direction. Since no movement in the rearward direction is permitted by spring element 70, drive wire 76 cannot activate the release mechanism to inadvertently release capsule 18 from delivery device 40 before the capsule 18 is anchored to the tissue site.

FIG. 5B illustrates the positioning of spring element 70 within groove 69 when controller 50 moves in the forward direction (indicated by arrow 58). Arrow 58 points toward elongated probe 46 of FIG. 2. When controller 50 is moved in the forward direction, spring element 70 moves to the portion of groove 69 in which groove channel 90A and groove channel 90B are communicatively coupled. The positioning of spring element 70 illustrated in FIG. 5B may, for example, correspond to the distal end of delivery device 40 anchoring capsule 18 to the tissue at the specific site.

FIG. 5C illustrates the positioning of spring element 70 within groove 69 after anchoring capsule 18 to the tissue at the specific site. As shown, spring element 70 moves into groove channel 90B after the movement of controller 50 in the forward direction. Groove 69 may be formed in such a manner that spring element 70 will be biased to being in groove channel 90B. For example, spring element 70 may be slightly bent into groove 90A during manufacturing and thus spring over to groove channel 90B in an attempt to straighten out after moving controller 50 in the forward direction.

Once in groove channel 90B, controller 50 may move in the rearward direction to the rear of groove channel 90B. As indicated above, the rear of groove channel 90B is further in the rearward direction (represented by arrow 59) than the rear of groove channel 90A. Rearward movement of controller 50 and spring element 70 in the rearward direction corresponds to the distal end of delivery device releasing capsule 18 from the delivery device 40. In this manner, groove 69 and spring element 70 prevent inadvertent release of capsule 18 from deliver device 40 by preventing controller 50 from initially moving in the rearward direction, which would engage the release mechanism. Although FIG. 5 is described with reference to groove 69 receiving a spring element 70, groove 69 may receive other elements to perform the same function as spring element 70. Moreover other types of grooves may be formed that perform the same function, i.e., preventing inadvertent release of capsule 18.

Figure 6:
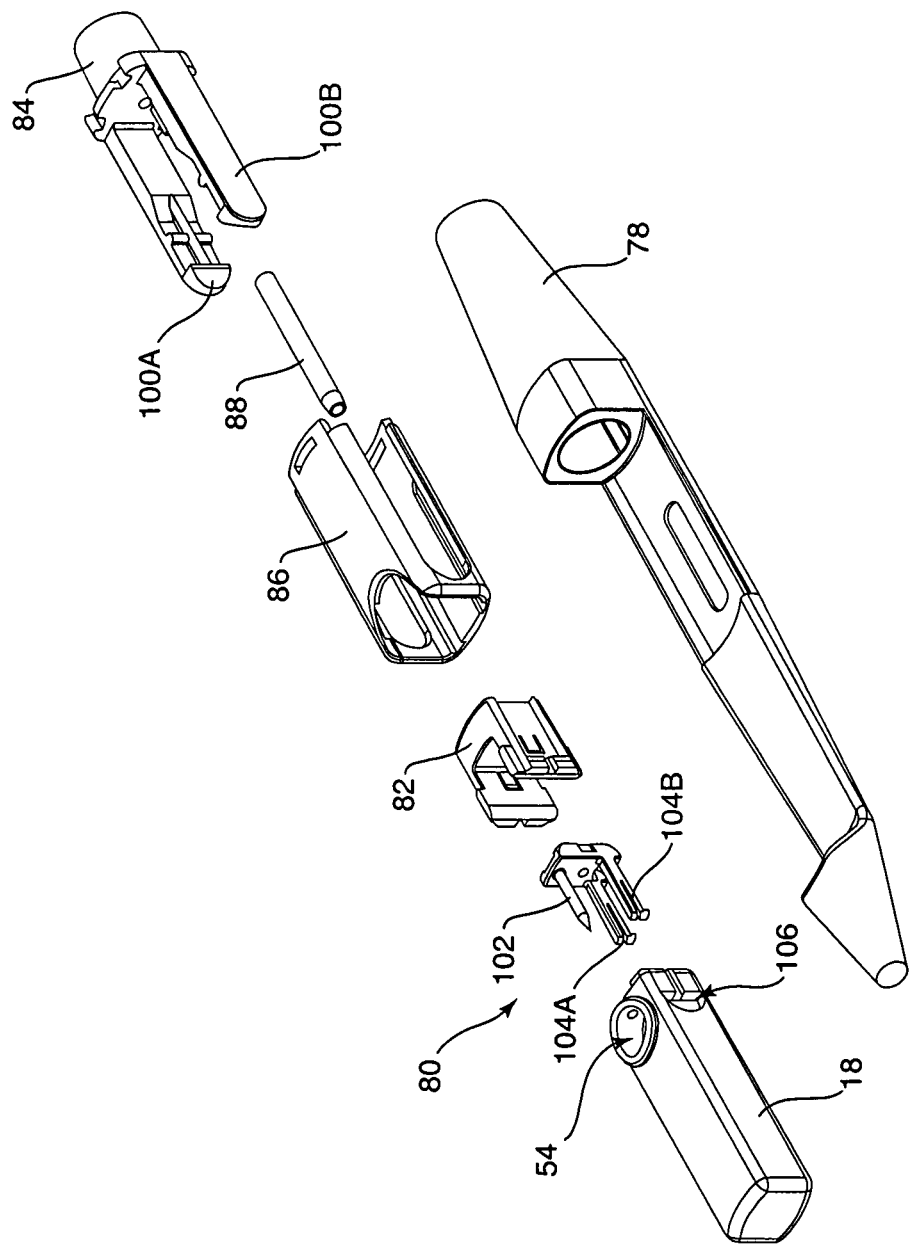
FIG. 6 is a schematic diagram illustrating an exploded view of a distal end of the delivery device of FIG. 2 in further detail.

FIG. 6 is a schematic diagram illustrating an exploded view of the distal end of delivery device 40 in further detail. The distal end of delivery device 40 includes a nose 78 that couples to an anchor element 80, a release mechanism 82 and a capsule coupling mechanism 84. Capsule coupling mechanism 84 fits into a capsule coupling housing 86. As illustrated in FIG. 3, capsule coupling mechanism 84 includes prongs 100A and 100B (collectively, "prongs 100"). Prong 100B of capsule coupling mechanism 84 engages with a channel 106 formed on capsule 18 to securely couple capsule 18 to delivery device 40 during delivery to a tissue location. Although only a single channel 106 is illustrated in FIG. 6, another similar channel exists on the opposite side of capsule 18 and engages with prong 100A of capsule coupling mechanism 84. Although only two prongs are illustrated in the example of FIG. 6, capsule coupling mechanism 84 may include more than two prongs that attach to capsule 18.

Anchor element 80 anchors capsule 18 to tissue that is suctioned into void 54 via suction delivered through vacuum channel 88. Anchor element 80 anchors capsule 18 to the tissue in void 54 during forward motion of controller 50. As an example, anchor element 80 may comprise a locking pin 102 that is driven through the tissue in void 54 in response to forward motion of controller 50. Anchor element 80 also includes tangs 104A and 104B (collectively, "tangs 104") that fit in channels within capsule 18 and couple the anchor element 80 to capsule 18. In this manner, anchor element 80 becomes a part of capsule 18. In some embodiments, anchor element 80 may be incorporated within capsule 18 and advance through the tissue in void 54. In this case, drive wire 74 anchor element 80 is always a part of the capsule 18.

After capsule 18 is anchored to the tissue, drive wire 74 engages release mechanism 82 to release capsule 18 from delivery device 40. In the example illustrated in FIG. 6, release mechanism 82 comprises a cam that interacts with capsule coupling mechanism 84 to release capsule 18. In particular, a ball 76 on a distal end of drive wire 74 (FIG. 3) engages with the cam during rearward motion to cause the cam to retract towards handle 44 causing prongs 100 of capsule coupling mechanism 84 to expand outwards. As the cam continues to retract toward handle 44, the prongs continue to expand outward until they disengage from channels 106 to release capsule 18. In this manner, the cam acts as a release mechanism that releases capsule 18 from delivery device 40.

Figure 7:
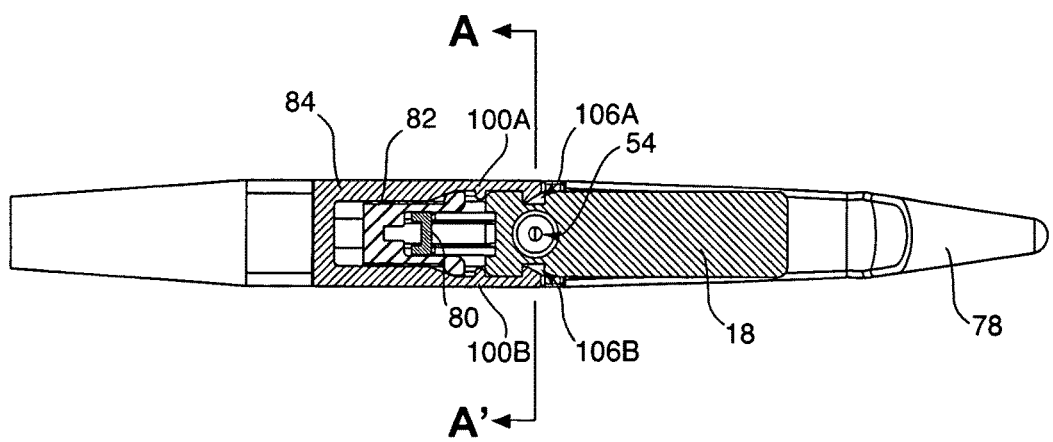
FIG. 7 is a cross-sectional top view of the distal end of delivery device shown in FIG. 6.

FIG. 7 is a cross-sectional view of a top of the distal end of delivery device 40. The top view illustrates the coupling of capsule 18 to the distal end of delivery device 40. Prongs 100A and 100B of capsule coupling mechanism couple capsule 18 to delivery device 40. In the embodiment illustrated in FIG. 7, capsule 18 is formed to include channels 106A and 106B that engage with prongs 100A and 100B, respectively, of capsule coupling mechanism 80.

During rearward motion of controller 50, drive wire 74 interacts with release mechanism 82 to release capsule 18. In particular, retraction of release mechanism 82 toward the handle of delivery device 40 causes prongs 100A and 100B to expand outward, eventually expanding outward far enough to release capsule 18 from delivery device 40. As illustrated in FIG. 7, prongs 100 of capsule coupling mechanism 84 are formed in a ramp-like manner. Release mechanism begins to move toward the thicker portion of the ramp of prongs 100 causing prongs 100 to be pushed outward, eventually releasing capsule 18 from delivery device 40.

Figure 8:
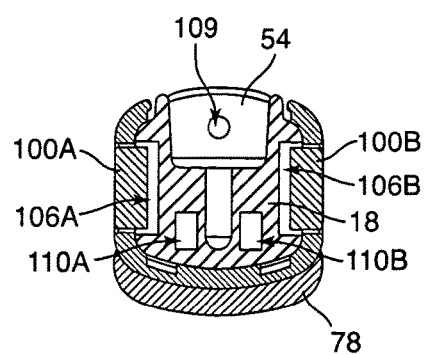
FIG. 8 is a cross-sectional view from A to A' of the distal end of a delivery device.

FIG. 8 is a cross-sectional front view of the distal end of delivery device 40 taken from A to A' as illustrated in FIG. 7. FIG. 8 illustrates the coupling between capsule 18 and capsule coupling mechanism 84. As shown in FIG. 8, capsule 18 includes a void 54 into which tissue is drawn in by the suction of vacuum 30 (FIG. 1). Void 54 includes an opening 109 through which locking pin 102 enters to anchor capsule 18 to tissue suctioned within void 54.

Capsule 18 includes anchor channels 110A and 110B that receive tangs, such as tangs 104 of anchor element 80 (FIG. 6) to attach anchor element 80 to capsule 18. In this manner, anchor element 80 becomes a part of capsule 18. Capsule 18 also includes coupling channels 106A and 106B ("coupling channels 106"). Prongs 100A and 100B of capsule coupling mechanism 84 engage with coupling channels 106A and 106B, respectively, to couple capsule to the distal end of delivery device 40.

During rearward motion of controller 50, drive wire 74 interacts with release mechanism 82 to cause prongs 100A and 100B to expand outward, eventually expanding outward far enough to release capsule 18 from delivery device 40. As described above, prongs 100 of capsule coupling mechanism 84 may be formed in a ramp-like manner. As release mechanism 82 begins to move toward the thicker portion of the ramp of prongs 100, prongs 100 begin to be push outward to release capsule 18 from delivery device 40.

Figure 9A:
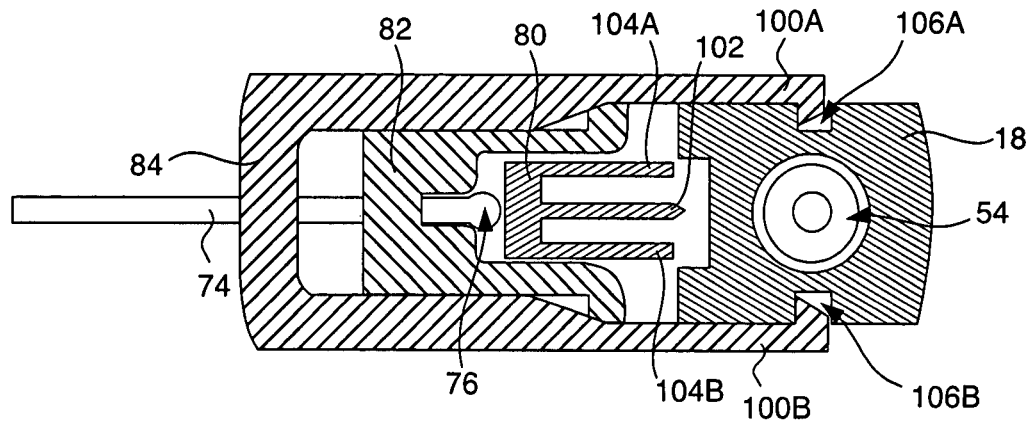
FIGS. 9A-9C are schematic diagrams illustrating exemplary operation of a distal end of an exemplary delivery device during various stages of delivery of a capsule.
Figure 9B:
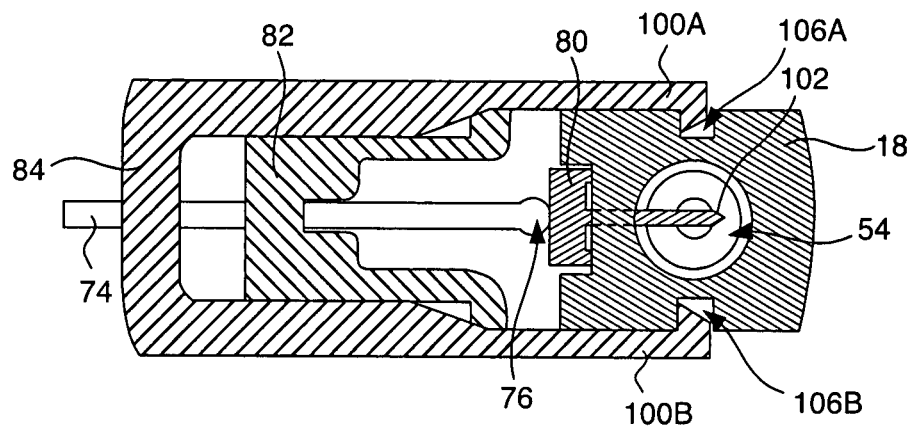
Figure 9C:
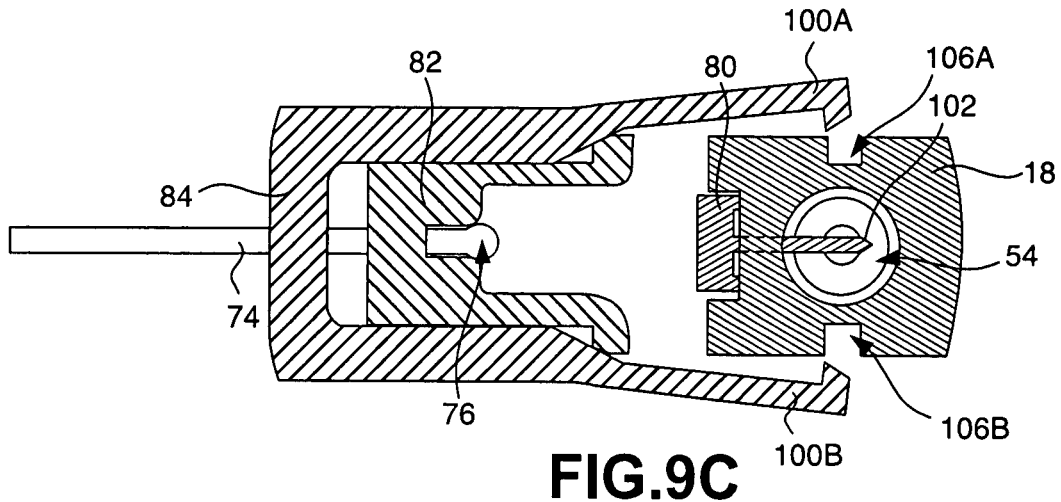

FIGS. 9A-9C are schematic diagrams illustrating exemplary operation of a delivery device for placing capsule 18 to tissue location within a patient. FIGS. 9A-9C illustrate the distal end of delivery device 40 during various stages of delivery of capsule 18. More specifically, FIG. 9A illustrates an initial configuration of the distal end of delivery device 40, FIG. 9B illustrates the distal end of delivery device 40 during anchoring of capsule 18 to the tissue at the site of interest, and FIG. 9C illustrates the distal end of delivery device 40 during release of capsule 18 from delivery device 40.

As illustrated in FIG. 9A, the initial configuration of the distal end of delivery device 40 is such that the anchor element 80 is not engaged with capsule 18. The initial configuration of the distal end of delivery device 40 is the configuration in which the delivery device would be upon initial receipt of the product. The configuration illustrated in FIG. 9A corresponds with the configuration of the handle portion described above with reference to FIG. 5A. In particular, spring element 70 is initially positioned within first groove channel 90A such that controller 50 is prevented from initially moving in the rearward direction. Since no movement in the rearward direction is permitted by spring element 70, drive wire 74 cannot activate the release mechanism to inadvertently release capsule 18 from delivery device 40 before the capsule 18 is anchored to the tissue site.

Upon identifying the appropriate location for placement of capsule 18, delivery device opens vacuum inlet 52 (FIG. 2). Vacuum inlet 52 receives sufficient suction pressure from vacuum 30 (FIG. 1) to draw a portion of esophageal tissue into a void 54 of capsule 18. Controller 50 is moved in a forward direction to cause delivery device 40 to anchor capsule 18 to the esophageal tissue. More specifically, the forward movement of controller 50 causes drive wire 74 to drive anchor element 80 through the tissue within void 54 to anchor capsule 18 to the wall of esophagus 14, as illustrated in FIG. 9B. The configuration illustrated in FIG. 9B corresponds with the configuration of the handle portion described above with reference to FIG. 5B. More specifically, spring element 70 moves to the portion of groove 69 in which spring channel 90A and spring channel 90B are communicatively coupled.

After capsule 18 is anchored to the wall of esophagus 14, controller 50 is moved in a rearward direction causing drive wire to retract toward handle 44 of delivery device 40. In particular, ball portion 76 of drive wire 74 engages with a release mechanism 82, such as a cam, during rearward motion to cause the cam to retract towards handle 44. In particular, ball portion 76 may be sized so that it cannot fit through a hole in release mechanism 82, thereby causing drive wire 74 to exert a pulling force on the release mechanism when the drive wire is pulled backward away from capsule 18. Release mechanism 82 begins to move toward the thicker portion of the ramp of prongs 100 causing prongs 100 to be pushed outward, eventually releasing capsule 18 from delivery device 40. The configuration illustrated in FIG. 9C corresponds with the configuration of the handle portion described above with reference to FIG. 5C. In particular, spring element 70 moves into groove channel 90B such that controller 50 may move in a rearward direction past the location of the initial position. Rearward movement of controller 50 and spring element 70 in the rearward direction corresponds to the distal end of delivery device releasing capsule 18 from the delivery device 40.

Figure 10A:
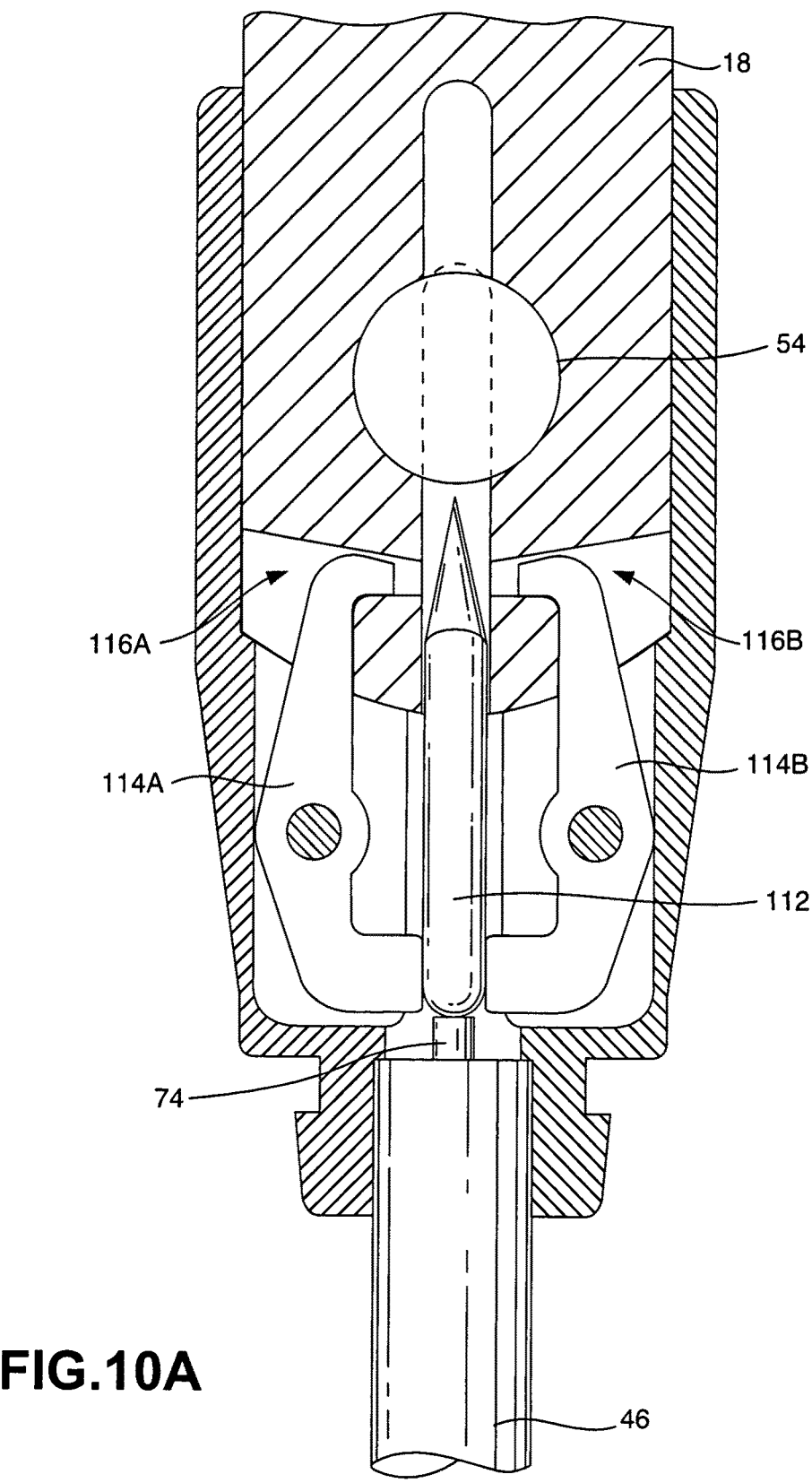
FIGS. 10A-10C are schematic diagrams illustrating exemplary operation of a distal end of another exemplary delivery device during various stages of delivery of a capsule.
Figure 10B:
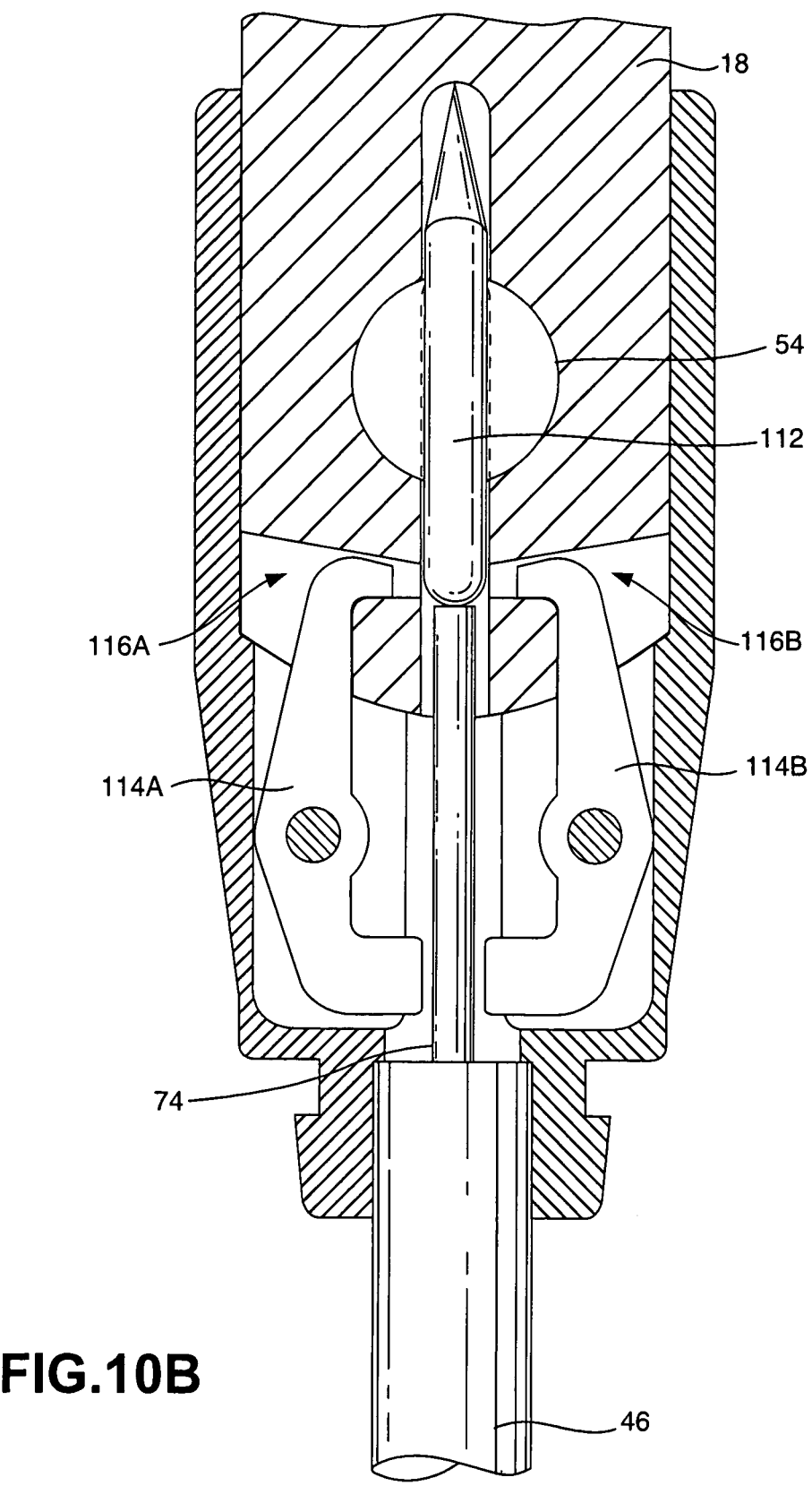
Figure 10C:
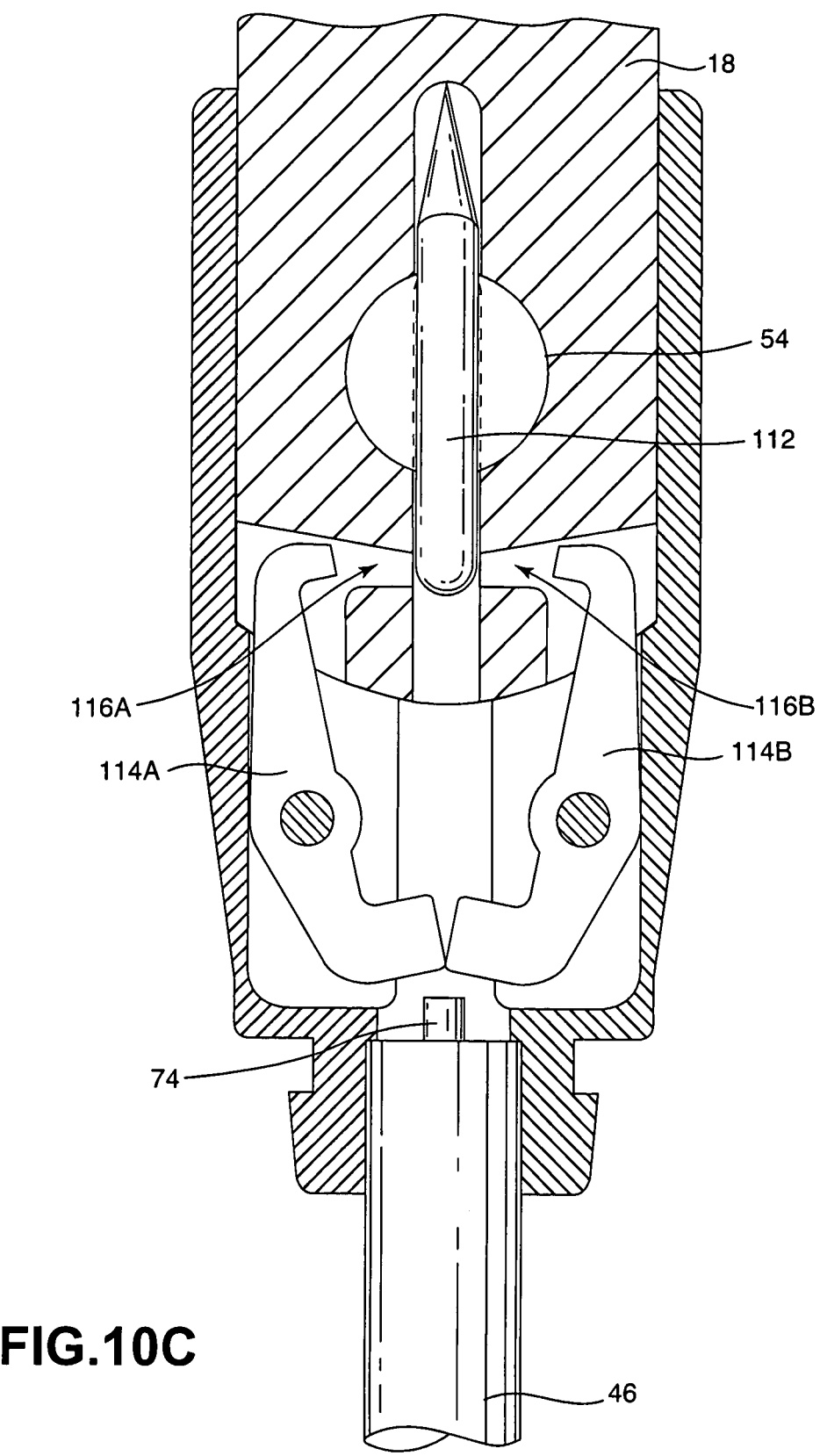

FIGS. 10A-10C are schematic diagrams illustrating exemplary operation of another exemplary delivery device for placing capsule 18 at a tissue location within a patient. FIGS. 10A-10C illustrate the distal end of the delivery device during various stages of delivery of capsule 18. More specifically, FIG. 10A illustrates an initial configuration of the distal end of the delivery device, FIG. 10B illustrates the distal end of the delivery device during anchoring of capsule 18 to the tissue at the site of interest, and FIG. 10C illustrates the distal end of the delivery device during release of capsule 18 from the delivery device.

The distal portion of the delivery device includes an anchor element 112 and a capsule coupling mechanism formed from latches 114A and 114B (collectively, "latches 114"). As illustrated in FIG. 10, latches 114 of the capsule coupling mechanism engage with respective ones of channels 116A and 116B formed on capsule 18 to securely couple capsule 18 to the delivery device during delivery of capsule 18 to a tissue location.

During the initial configuration illustrated in FIG. 10A, anchor element 112 separates latches 114. In particular, the ends of latches 114 not coupled to capsule 18 are separated by anchor element 112. Anchor element 112 is used to anchor capsule 18 to tissue that is suctioned into void 54. Anchor element 112 is pushed forward by drive wire 74 during forward movement of controller 50 to anchor capsule 18 to the tissue in void 54. FIG. 10B illustrates the distal end of the delivery device after anchor element 112 is pushed forward. As shown in FIG. 10B, anchor element 112 no longer separates latches 114. However, drive wire 74 is located between latches 114 during movement in the forward direction and thus continues to separate latches 114. In one embodiment, drive wire 74 and anchor element 112 are of substantially the same thickness and diameter.

After capsule 18 is anchored to the tissue, drive wire 74 retracts towards handle 44. Drive wire 74 continues to retract until it no longer separates latches 114. FIG. 10C illustrates the distal end of the delivery device after retraction of drive wire 74. With nothing left separating the ends of latches 114 that are not coupled to capsule 18, latches 114 open to release capsule 18. In one embodiment, the latches are biased so that the ends not coupling to capsule 18 push toward one another. The ends of latches 114 may, for example, be biased to push toward one another using a spring mechanism that causes the portion of latches 114 separated by drive wire 74 to come together. Latches 114 may be biased using other biasing means, such as a magnet. This in turn causes the portion of latches 114 that engage the capsule to be pushed outward, i.e., away from one another. In this manner, movement of drive wire 74 in the rearward direction activates the release mechanism, i.e., the spring mechanism in this example. The outward movement causes latches 114 to release capsule 18 at the specific site.

Figure 11:
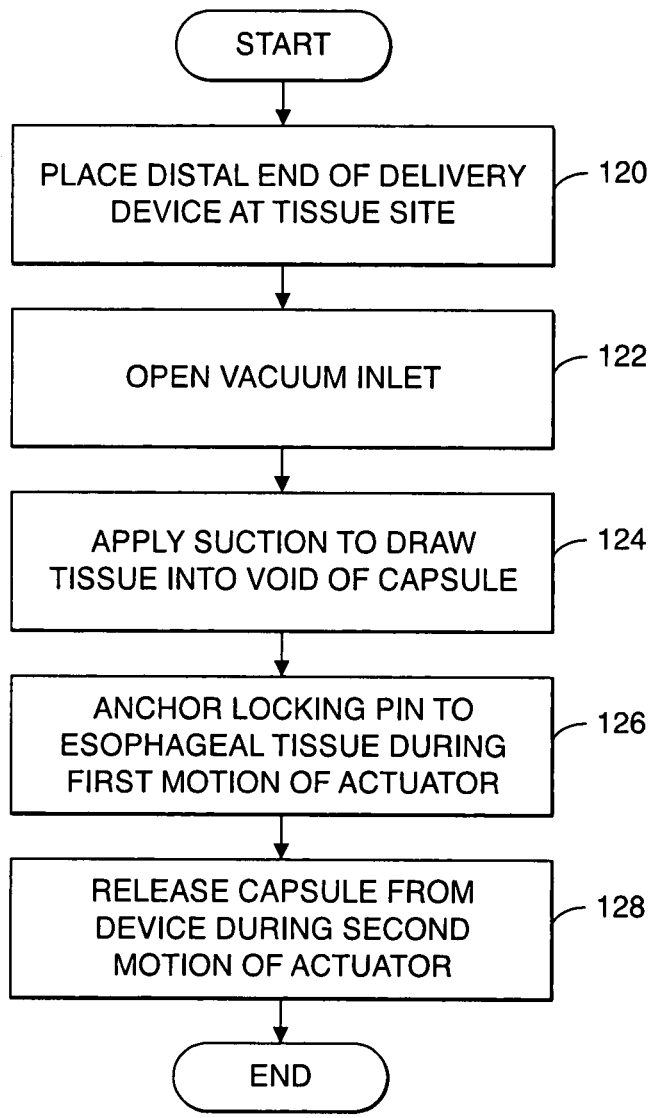
FIG. 11 is a flow diagram illustrating exemplary operation of a delivery device placing a capsule at a location within a patient.

FIG. 11 is a flow diagram illustrating exemplary operation of delivery device 40 placing a capsule 18 to an esophagus 14 of the patient. Initially, delivery device 40 places the distal end of delivery device 40 at tissue at a site of interest (120). In particular, the distal end of delivery device 40 enters esophagus 14, via either the nasal or oral cavity, and extends through esophagus 14 to the LES.

Upon identifying the appropriate location for anchoring of capsule 18, delivery device 40 opens vacuum inlet 28 (122). Delivery device 40 receives suction pressure from vacuum 30 to draw esophageal tissue into a void of capsule 18 (124). Delivery device 40 anchors capsule 18 to the wall of esophagus 14 during a first motion of an actuator (126). For example, delivery device 40 may advance drive wire 74 to drive a locking pin through the esophageal tissue in the void of capsule 18 to anchor the capsule 18 when controller 50 is advanced in a forward direction.

After anchoring capsule 18 to esophagus 14, delivery device releases capsule 18 during a second motion of the actuator, thereby leaving capsule 18 anchored to esophagus 14 (128). For example, movement of controller 50 may cause drive wire 74 to activate a release mechanism to release capsule 18. In one embodiment, rearward motion of drive wire 74 may engage a cam, which causes prongs 100 of a capsule coupling mechanism 84 to expand and detach from capsule 18. In another embodiment, drive wire 74 may separate latches 114 (FIG. 10) that are spring biased toward one another, and rearward motion of the drive wire 74 may result in drive wire 74 no longer separating latches 114. In this case, latches 114 push toward one another to release capsule 18.

In some embodiments, the first and second motion may be motion in substantially opposite directions. For example, the actuator may activate the anchor element during a forward motion and activate a release mechanism during a rearward motion. In other embodiments, the first and second motion may be motion in substantially the same direction. For example, the actuator may activate an anchor element during a forward motion to a first position and activate the release mechanism during a forward motion to a second position.

While anchored on the wall of esophagus 14, one or more sensors within capsule 18 obtain measurements, such as acidity measurements, within esophagus 14, and capsule 18 relays the measurements to receiver 20 via wireless telemetry. In some embodiments, capsule 18 may transmit the measurements to receiver 20 and/or to an external or implanted therapy device, such as an electrical neurostimulator or a drug delivery device. A neurostimulator, drug delivery device, or other therapeutic device may be responsive to measurements obtained by capsule 18 to delivery therapy based on the measurements. Alternatively, a neurostimulator, drug delivery device, or other therapeutic device may be responsive to commands transmitted by receiver 20 to the device, in which case receiver 20 generates the commands based on the measurements obtained by capsule 18.

Although the embodiments described in this disclosure relate to placement of a capsule for sensing acidity of esophagus of the patient, the techniques of the disclosure may be applied for delivery of other types of sensors to different body lumens, tissue locations or organs within a patient. Moreover, the techniques of this disclosure may be used to place other therapeutic devices, such as neurostimulators, drug delivery devices, drug release devices, or other devices to locations within patient. The techniques and system of this disclosure may be used to place in the stomach or other location in the gastrointestinal tract an intra-luminal device for gastrointestinal electrical stimulation such as one of such devices described in U.S. application Ser. No. 10/801,230, published as Publication No. 2005/0209653 to Herbert, et al., the entire content of which is incorporated herein by reference. For example, such a system may be used to sense physiological conditions within different body lumens, such as the esophagus, stomach, intestines, urethra, bladder, or colon. In urinary tract applications, for example, the system may be adapted for urodynamic testing, urinalysis, or other diagnostic evaluations pertinent to the urinary tract, e.g., as described in U.S. Published Patent Application No. 2005/0245840 to Christopherson et al., the entire content of which is incorporated herein by reference. Moreover, the techniques are not limited to application for monitoring associated with any particular disorder, condition or affliction. As further examples, a monitoring device in accordance with the techniques of this disclosure can be used to monitor other types of physiological conditions, such as conditions indicative of pregnancy, ovulation, or the condition of a fetus.

The preceding specific embodiments are illustrative of the practice of the techniques of this disclosure. It is to be understood, therefore, that other expedients known to those skilled in the art or disclosed herein may be employed without departing from the scope of the following claims.

The invention claimed is:

1. A device comprising:
    an elongated probe configured to carry an implantable capsule for deployment within a patient;
    an anchor element configured to anchor the capsule to tissue within the patient;
    a vacuum chamber;
    a release mechanism configured to release the capsule from the probe; and
    an actuator configured to activate the anchor element to cause the anchor element to anchor the capsule to the tissue during a first motion of the actuator, and activate the release mechanism to vent the vacuum chamber and to release the capsule from the probe during a second motion of the actuator.

2. The device of claim 1, wherein the first motion and the second motion comprise motion in substantially opposite directions.

3. The device of claim 2, wherein the actuator activates the anchor element during a forward motion and activates the release mechanism during a rearward motion.

4. The device of claim 1, wherein the first motion and the second motion comprise motion in substantially the same direction.

5. The device of claim 4, wherein the actuator activates the anchor element during a forward motion of the actuator to a first position and activates the release mechanism during a forward motion of the actuator to a second position.

6. The device of claim 1, further comprising a capsule coupling mechanism configured to couple the capsule to a distal end of the probe, wherein the release mechanism causes the capsule coupling mechanism to release the capsule during the second motion of the actuator.

7. The device of claim 6, wherein the capsule coupling mechanism includes one or more prongs configured to couple to the capsule, and further wherein the release mechanism causes the prongs to release the capsule during the second motion of the actuator.

8. The device of claim 6, wherein the capsule coupling mechanism includes:
a first latch configured to couple to the capsule at a first end of the first latch; and
a second latch configured to couple to the capsule at a first end of the second latch, wherein second ends of the first and second latches are biased such that the second ends push toward one another; and
further wherein the actuator separates the second ends of the first and second latches.

9. The device of claim 8, wherein the actuator, during a rearward movement, retracts far enough to no longer separate the second ends of the latches to cause the second ends of the latches to push together to open the first ends of the latches to release the capsule.

10. The device of claim 8, wherein the second end of each of the first and second latches is biased by one of a spring element and a magnet.

11. The device of claim 1, wherein the anchor element comprises a locking pin, and further wherein the actuator engages with the locking pin to advance the locking pin through the tissue during the first motion.

12. The device of claim 1, further comprising:
a controller that advances in a forward and rearward motion to control the motion of the actuator; and
a locking mechanism that prevents the controller from moving in the rearward motion prior to moving in the forward motion.

13. The device of claim 12, wherein the locking mechanism comprises:
a groove within a handle of the device, wherein the groove includes a first channel and a second channel, the first channel being of a shorter distance than the second channel; and
a spring element within the groove, wherein the spring element moves from the first channel to the second channel after the first motion.

14. The device of claim 12, wherein the locking mechanism comprises a first locking mechanism, and further comprising a second locking mechanism that prevents movement of the controller in any direction.

15. The device of claim 1, wherein the actuator comprises a drive wire.

16. The device of claim 15, further comprising:
a drive wire adaptor that couples with the drive wire to drive the drive wire in the first and second motion, wherein the drive wire adaptor includes a first section of a first diameter and as second section of a second diameter, the first section having a larger diameter than the second section;
a vacuum seal that includes a central aperture for seating the drive wire adaptor, wherein the first portion of the drive wire adaptor is seated in the central aperture during the first motion and the second section of the drive wire adaptor is seated in the central aperture during the second motion,
wherein the vacuum chamber is formed when the first section of the drive wire adaptor is seated in the central aperture and is vented when the second section of the drive wire is seated in the central aperture.

17. The device of claim 1, further comprising a vacuum inlet that couples to the vacuum chamber, wherein the device is configured to provide suction to draw the tissue into a void of the capsule.

18. A method comprising:
carrying an implantable capsule using an elongated probe of a device for deployment within a patient;
forming a vacuum chamber to draw tissue within the patient into a void of the capsule;
anchoring the implantable capsule to the tissue within the patient during a first motion of an actuator of the device; and
venting the vacuum chamber and releasing the capsule from the device during a second motion of the actuator.

19. The method of claim 18, wherein:
anchoring the capsule to the tissue during the first motion of the actuator comprises anchoring the capsule to the tissue during a forward motion; and
releasing the capsule from the device during the second motion of the actuator comprises releasing the capsule from the device during a rearward motion.

20. The method of claim 19, further comprising configuring the device to prevent the rearward motion of the actuator prior to the forward motion of the actuator.

21. The method of claim 18, wherein:
anchoring the capsule to the tissue during the first motion of the actuator comprises anchoring the capsule to the tissue during a forward motion of the actuator to a first position; and
releasing the capsule from the device during the second motion of the actuator comprises releasing the capsule from the device during a forward motion of the actuator to a second position.

22. The method of claim 18, further comprising coupling the capsule to a distal end of the device using one or more prongs, wherein releasing the capsule from the device comprises disengaging the prongs to release the capsule.

23. The method of claim 18, further comprising coupling the capsule to a distal end of the device using a first latch and a second latch, wherein each of the latches comprises a first end that couples to the capsule and a second end that is biased to push toward the other one of the latches.

24. The method of claim 23, wherein the actuator separates the second ends of the first and second latches, and further wherein releasing the capsule from the device comprises retracting the actuator far enough to no longer separate the second ends of the latches to cause the second ends of the latches to push together to open the first ends of the latches to release the capsule.

25. The method of claim 18, wherein anchoring the capsule to the tissue comprises advancing a locking pin through the tissue during the first motion of the actuator.

26. The method of claim 18, wherein the capsule includes a sensor and further comprising:
measuring one or more parameters of the patient via the sensor of the capsule; and
transmitting the measured parameters from the capsule to a receiver.

27. The method of claim 18, wherein the tissue comprises the esophagus.

28. The method of claim 18, further comprising providing suction to the tissue to draw a portion of the tissue into a void of the capsule, wherein anchoring the capsule to the tissue comprises anchoring the capsule to the portion of the tissue drawn into the void of the capsule.

29. A device comprising:
   means for carrying an implantable capsule for deployment within a patient;
   means for drawing tissue within the patient into a void of the capsule;
   means for anchoring the capsule to the tissue within the patient;
   means for releasing the capsule from the carrying means; and
   means for activating the anchoring means to anchor the capsule to the tissue during a first motion of the activating means and releasing the drawing means and activating the releasing means to release the capsule from the carrying means during a second motion of the activating means.

30. The device of claim 29, further comprising means for coupling the capsule to the carrying means, wherein the releasing means causes the coupling means to release the capsule during the second motion of the activating means.

31. The device of claim 29, further comprising:
   means for controlling motion of the activating means; and
   means for locking the controlling means to prevent the controlling means from moving in a rearward motion prior to moving in a forward motion.

32. The device of claim 29, wherein the activating means comprises a drive wire.

33. A system comprising:
   a delivery apparatus comprising:
      an elongated probe configured to carry an implantable capsule for deployment within a patient,
      a vacuum chamber,
      a release mechanism configured to release the capsule from the probe and an actuator, and
      an actuator to control delivery of the capsule; and
   an anchor element configured to anchor the capsule to tissue within the patient, wherein the actuator is configured to activate the anchor element to cause the anchor element to anchor the capsule to the tissue during a first motion of the actuator, and to vent the vacuum chamber and activate the release mechanism to release the capsule from the probe during a second motion of the actuator.

34. The system of claim 33, further comprising the implantable capsule coupled to the elongated probe.

35. The system of claim 34, wherein the anchor element is incorporated within the implantable capsule.

\* \* \* \* \*